(12) United States Patent
Predick

(10) Patent No.: US 11,020,241 B2
(45) Date of Patent: Jun. 1, 2021

(54) EXPANDABLE LATERAL SPINE CAGE WITH REVERSE DOVETAIL CONFIGURATION

(71) Applicant: Life Spine, Inc., Huntley, IL (US)

(72) Inventor: Daniel P. Predick, West Lafayette, IN (US)

(73) Assignee: LIFE SPINE, INC., Huntley, IL (US)

(*) Notice: Subject to any disclaimer, the term of this patent is extended or adjusted under 35 U.S.C. 154(b) by 221 days.

(21) Appl. No.: 15/440,976

(22) Filed: Feb. 23, 2017

(65) Prior Publication Data
US 2017/0239063 A1 Aug. 24, 2017

Related U.S. Application Data

(60) Provisional application No. 62/298,951, filed on Feb. 23, 2016.

(51) Int. Cl.
*A61F 2/44* (2006.01)
*A61F 2/30* (2006.01)

(52) U.S. Cl.
CPC .......... *A61F 2/447* (2013.01); *A61F 2/30771* (2013.01); *A61F 2/4455* (2013.01);
(Continued)

(58) Field of Classification Search
CPC ...... A61F 2/447; A61F 2/4455; A61F 2/4425; A61F 2/4611; A61F 2/30771; A61F 2002/443; A61F 2002/4475; A61F 2002/30579; A61F 2002/30387; A61F 2002/30385; A61F 2002/30326; A61F 2002/30598; A61F 2002/3082;
(Continued)

(56) References Cited

U.S. PATENT DOCUMENTS

| 8,057,548 B2* | 11/2011 | Abernathie | A61F 2/4455 623/17.16 |
| 8,257,441 B2* | 9/2012 | Duplessis | A61F 2/4425 623/17.15 |
| 8,535,380 B2* | 9/2013 | Greenhalgh | A61F 2/447 623/17.15 |
| 8,545,567 B1 | 10/2013 | Krueger | |

(Continued)

OTHER PUBLICATIONS

Search Report for International Application No. PCT/US2017/019206, dated Jun. 16, 2017, 10 pages.

*Primary Examiner* — Kevin T Truong
*Assistant Examiner* — Tracy L Kamikawa
(74) *Attorney, Agent, or Firm* — Foley & Lardner LLP

(57) ABSTRACT

A spinal interbody implant includes a two-component cage and expander. The two-component cage, when assembled, accepts the expander through a reverse dovetail configuration between the assembled cage and the expander. The expander has a pair of legs that move within and along lateral channels formed by and between the two cage components for increasing the height of the two cage components relative to one another. The amount of expansion of the cage is determined by the height of the pair of expander legs. The cage accepts different expanders each having pairs of legs of different heights in order to provide different amounts of cage expansion and thus the interbody implant. The front of each expander leg is arch shaped for reception in the lateral channels of the assembled cage and to progressively expand the two cage components relative to one another as the expander is received by the assembled cage.

20 Claims, 14 Drawing Sheets

(52) U.S. Cl.
CPC .................. *A61F 2002/3082* (2013.01); *A61F 2002/30326* (2013.01); *A61F 2002/30385* (2013.01); *A61F 2002/30387* (2013.01); *A61F 2002/30398* (2013.01); *A61F 2002/30476* (2013.01); *A61F 2002/30515* (2013.01); *A61F 2002/30579* (2013.01); *A61F 2002/30593* (2013.01); *A61F 2002/30594* (2013.01); *A61F 2002/30616* (2013.01); *A61F 2002/30785* (2013.01); *A61F 2002/30841* (2013.01)

(58) Field of Classification Search
CPC .. A61F 2002/30785; A61F 2002/30841; A61F 2002/30398; A61F 2002/30476; A61F 2002/30515; A61F 2002/30593; A61F 2002/30616

See application file for complete search history.

(56) References Cited

U.S. PATENT DOCUMENTS

| | | | |
|---|---|---|---|
| 8,585,761 B2* | 11/2013 | Theofilos | A61F 2/44 623/17.11 |
| 8,673,011 B2* | 3/2014 | Theofilos | A61F 2/44 623/17.16 |
| 8,715,351 B1 | 5/2014 | Pinto | |
| 2003/0074063 A1 | 4/2003 | Gerbec et al. | |
| 2005/0060034 A1 | 3/2005 | Berry et al. | |
| 2013/0158667 A1* | 6/2013 | Tabor | A61F 2/4455 623/17.16 |
| 2013/0211526 A1* | 8/2013 | Alheidt | A61F 2/442 623/17.16 |
| 2014/0243982 A1* | 8/2014 | Miller | A61F 2/447 623/17.16 |
| 2014/0257484 A1* | 9/2014 | Flower | A61F 2/447 623/17.15 |
| 2015/0182346 A1* | 7/2015 | Emerick | A61F 2/4465 623/17.15 |

* cited by examiner

EXPANDABLE LATERAL SPINE CAGE WITH REVERSE DOVETAIL CONFIGURATION

CROSS-REFERENCE TO RELATED APPLICATIONS

This U.S. non-provisional patent application claims the benefit of and/or priority under 35 U.S.C. § 119(e) to U.S. provisional patent application Ser. No. 62/298,951 filed Feb. 23, 2016 titled "Expandable Lateral Spine Cage With Reverse Dovetail Configuration," the entire contents of which is specifically incorporated herein by reference.

FIELD OF THE INVENTION

The present invention relates to orthopedic implants for the spine and, particularly, to interbody cages for spinal fusion.

BACKGROUND OF THE INVENTION

Many people contend with spine issues as a result of age, disease, and trauma, as well as congenital and acquired complications and conditions. While some of these issues can be alleviated without surgery, other issues respond better to surgery. In some cases, surgery may include placing an implant into the spine. If vertebral fusion is required, a spine implant known as an interbody cage along with bone graft or bone graft material may be used.

An interbody cage is a device that is placed in the disc space between adjacent vertebrae of a recipient's spine. The interbody cage includes openings, bores, and/or is porous or the like to permit the introduction and/or carrying of bone graft/bone graft material in order to allow the bone graft/bone graft material to grow from one vertebra through the interbody cage and into the adjacent vertebra. Such interbody cages provide excellent fixation such that most recipients do not require additional implants such as plates and/or bone screws.

In some instances it is desirable that the interbody cage be able to expand once it has been implanted in the spine. Various expandable interbody cages have been designed, but are either complicated in their expansion mechanisms, are not reliable once implanted, or suffer from other expansion issues.

It is therefore an object of the present invention to provide an expandable interbody cage that overcomes the deficiencies of the prior art.

SUMMARY OF THE INVENTION

A spinal interbody cage implant includes a two-component cage and expander. The two-component cage, when assembled, accepts the expander through a reverse dovetail configuration between the cage and the expander. The expander has a pair of legs that move within and along lateral channels formed by and between the two cage components in order to expand (i.e. increase the height of) the two cage components relative to one another.

The amount of expansion (height increase) of the cage is determined by the height of the pair of legs of the expander. The cage accepts different expanders each having pairs of legs of different heights in order to provide different amounts of expansion (heights) of the cage and thus the interbody cage implant.

The two components of the cage, when assembled, define an end having an opening with upper and lower sidewalls that are angled inwardly in a generally trapezoidal manner. An end of the expander has upper and lower sidewalls that are angled upwardly in a generally trapezoidal manner, opposite to that of the generally trapezoidal end opening of the assembled cage. The end of the expander is thus shaped for reception in the end opening of the assembled cage in a reverse dovetail configuration.

The front of each leg of the expander is in the shape of an arch for reception in the lateral channels of the assembled cage and to progressively expand the two cage components relative to one another as the expander is inserted into/received by the assembled cage.

The lower component has a central opening with a configured sidewall extending generally transverse to the plane of the lower component. The upper component has a central opening separated by a cross member with a configured sidewall extending generally transverse to the plane of the upper component. When the upper and lower components are assembled, the configured sidewall of the upper component fits within the sidewall of the lower component. In addition, the upper component has openings in its upper surface that receive the configured sidewall of the lower component.

The upper component includes a plurality of spikes, projections or the like that extend generally upwards from the upper surface of the upper component, preferably, but not necessarily, about the central opening. The lower component includes a plurality of spikes, projections or the like that extend generally downwards from the lower surface of the lower component, preferably, but not necessarily, about the central opening.

The lower component has an upwardly curved lower front surface and an angled upper rear surface. The upper component has a downwardly curved upper front surface and an angled lower rear surface. The upwardly curved lower front surface of the lower component and the downwardly curved upper surface of the upper component provide an angled nose that allows easy insertion of the cage implant into a space between adjacent vertebrae.

The spinal interbody cage implant may be used in a lateral insertion procedure, a posterior insertion procedure, or an anterior insertion procedure.

Further aspects of the present invention will become apparent from consideration of the drawings and the following description of a form of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate a form of the present invention, wherein.

DETAILED DESCRIPTION OF THE INVENTION

Figure 1:
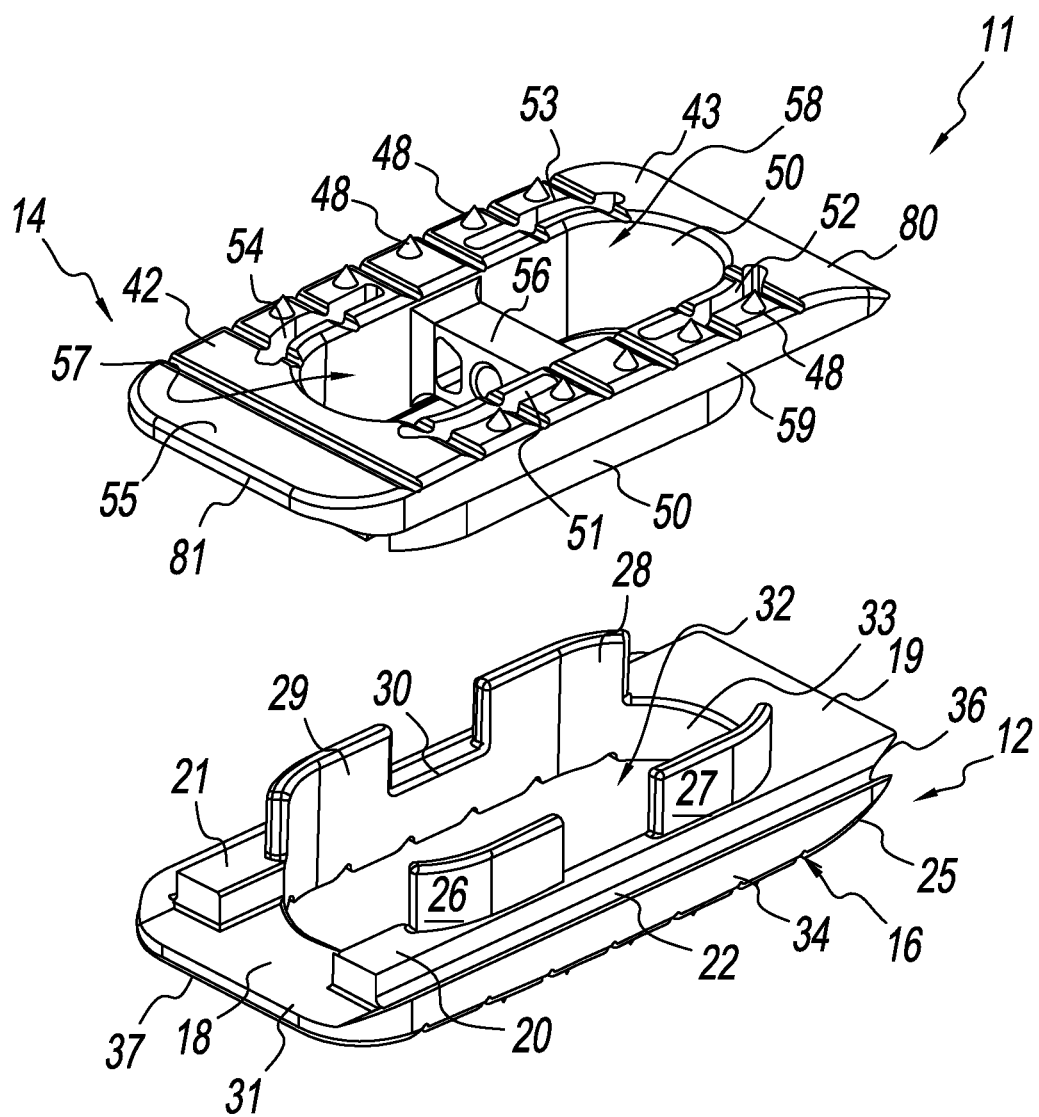
FIG. 1 is an exploded isometric view of the two components of the cage of an exemplary spine cage implant fashioned in accordance with the present principles.

Referring to the figures, there is depicted an exemplary form of the present expandable spine cage implant, generally designated 10. The expandable spine cage implant 10 is made from a biocompatible material such as, but not limited to, titanium, stainless steel, an alloy of titanium or steel, or otherwise. The expandable spine cage implant 10 is characterized by a cage 11 and an expander 66, the cage 11 is composed of two components, a first, lower, or inferior component 12 (collectively, lower component 12) and a second, upper, or superior component 14 (collectively, upper component 14), the nomenclature first and second being arbitrary. The expandable spine cage implant 10 may be used between any two vertebrae of the spine.

Figure 2:
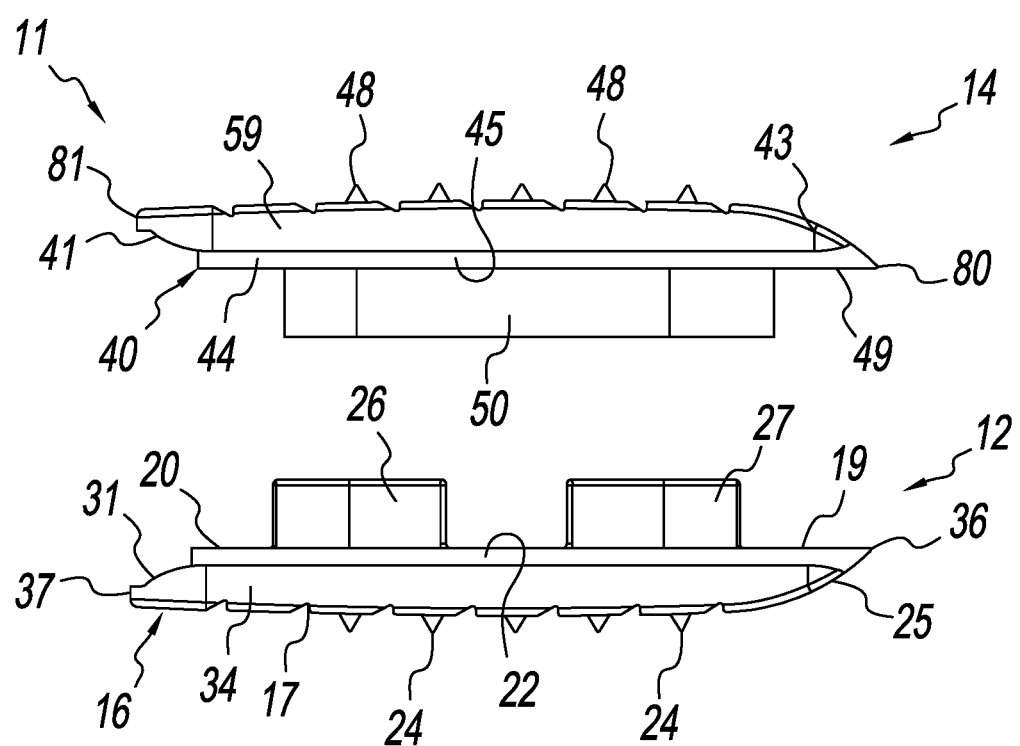
FIG. 2 is an exploded side (lateral) view of the two components shown in FIG. 1.
Figure 3:
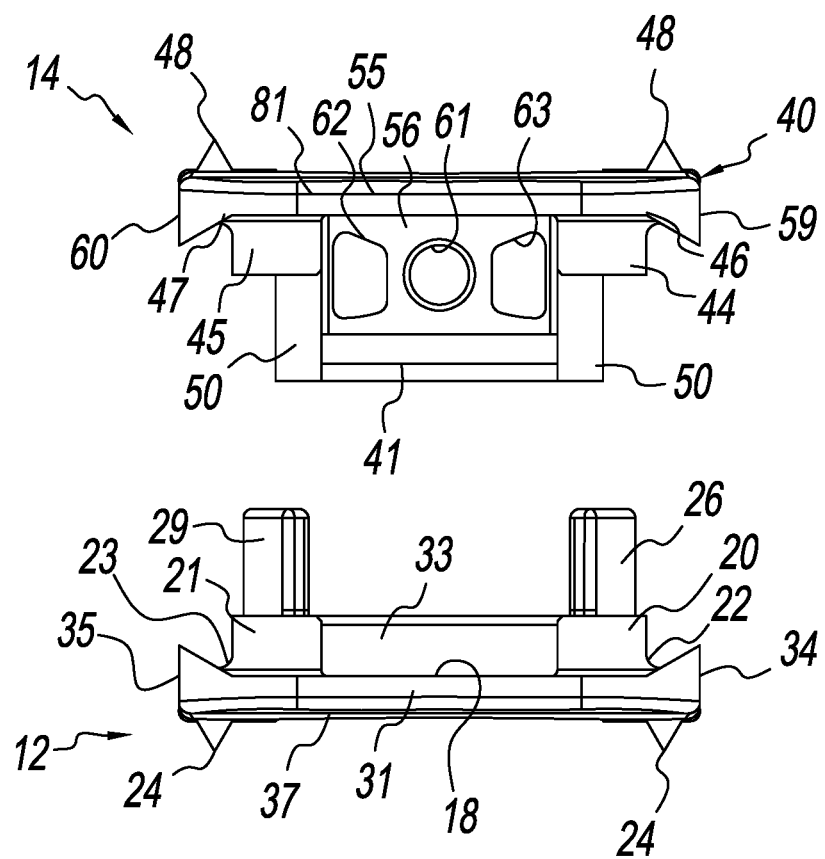
FIG. 3 is an exploded end view of the two components shown in FIG. 1.
Figure 4:
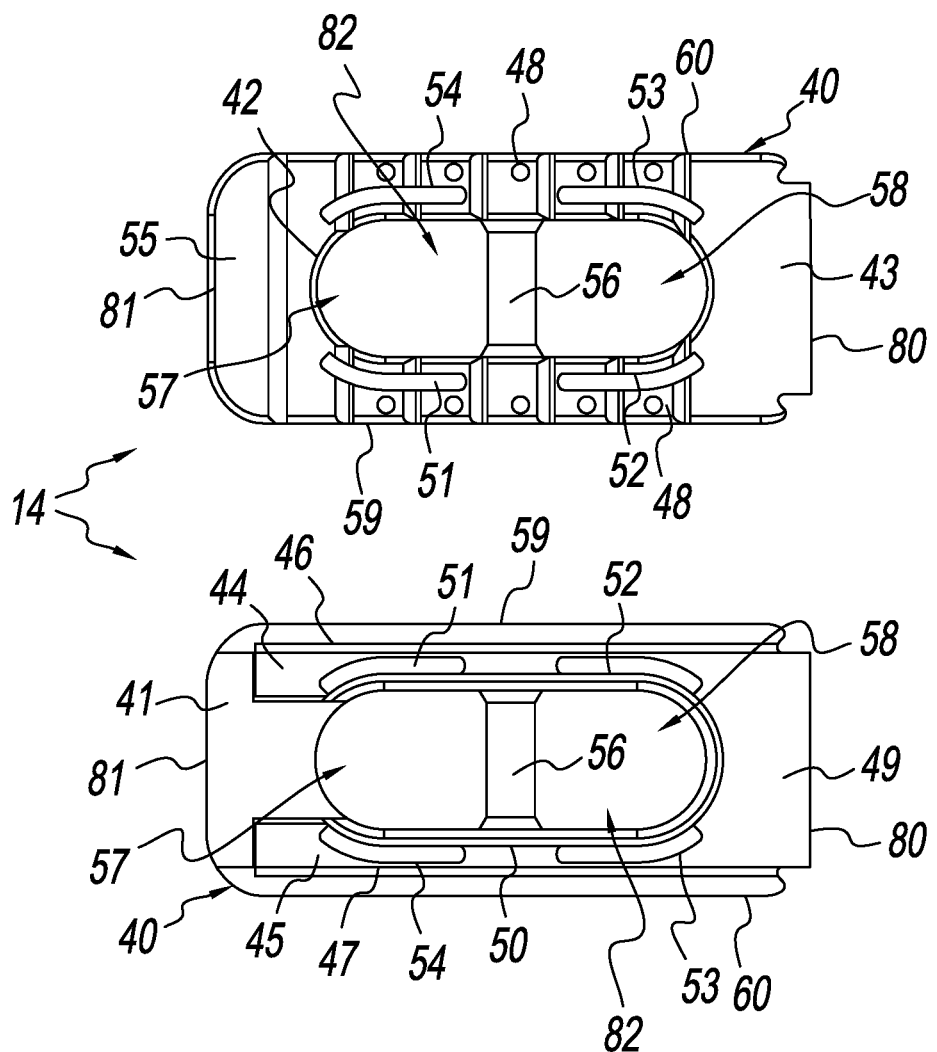
FIG. 4 is a top plan view of the two components shown in FIG. 1 presented side-by-side.
Figure 5:
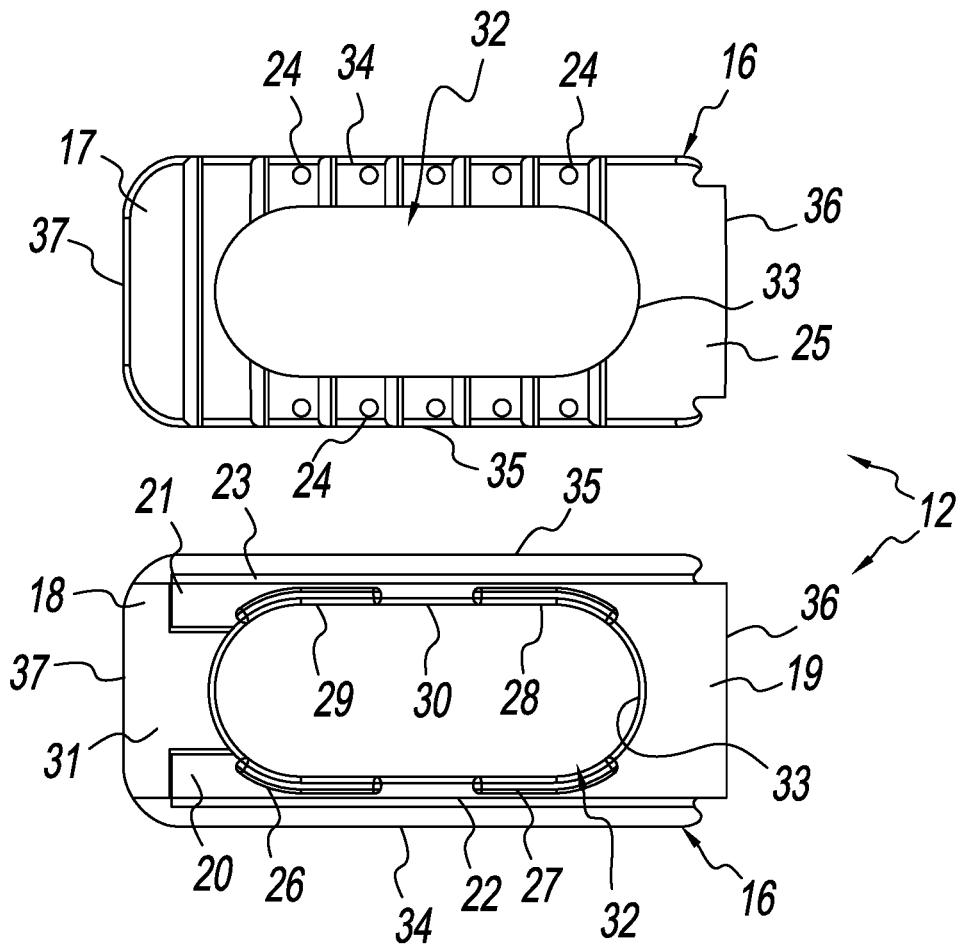
FIG. 5 is a bottom plan view of the two components shown in FIG. 1 presented side-by-side.
Figure 6:
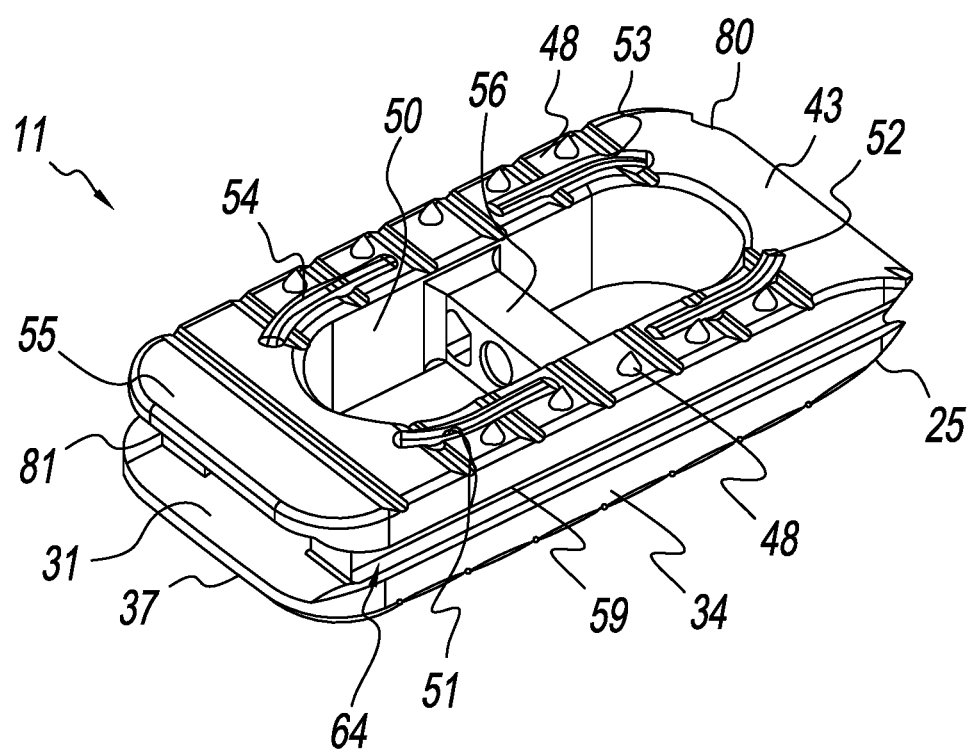
FIG. 6 is an isometric upper front lateral view of the assembled cage of the present spine cage implant.
Figure 7:
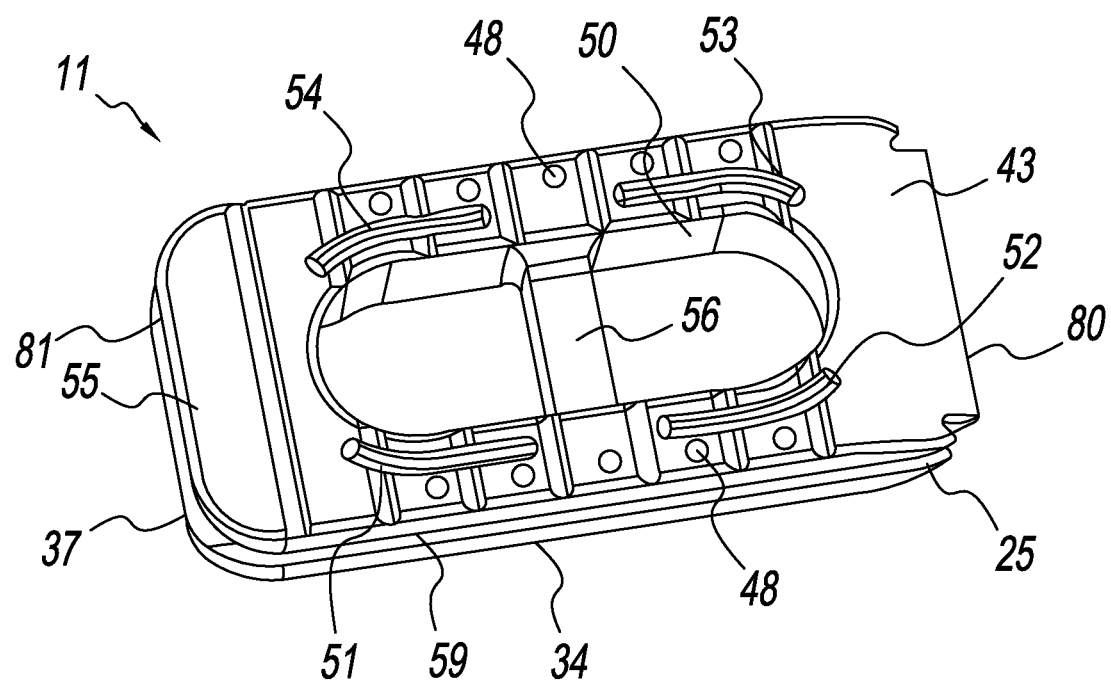
FIG. 7 is an isometric upper view of the assembled cage of the present spine cage implant.

FIGS. 1-3 depict the lower component 12 and the upper component 14 in exploded views, while FIGS. 4-5 depict top plan and bottom plan views of the lower and upper components 12, 14. The exploded views show how the two components are assembled or received on one another thereby forming the cage 11. The plan views show details of the two cage components.

The lower component 12 is characterized by a body 16 of a generally rectangular shape having a generally planar lower or inferior surface 17 and a generally planar upper or superior surface 18. The body 16 has a first, generally elongated lateral side 34 and a second, generally elongated lateral side 35, the nomenclature first and second being arbitrary. A first end 36 of the body 16 has a generally planar platform 19 at its upper/superior surface and its lower/inferior surface 25 curved upwardly, while a second end 37 of the body 16 has a generally planar lower/inferior surface and an upwardly angled portion 31 that meets with its generally planar upper/superior surface 19, the nomenclature first and second being arbitrary. The body 16 further has a central opening, window or the like 32 that is generally oval in shape. The opening 32 is provided with a configured sidewall 33 that extends about a majority of the opening 32, with the exception of an area proximate the second end 37.

The configured sidewall 33 has a first portion 26 situated proximate the second end 37 and lateral side 34 of the body 16 that extends upwardly or transverse to the plane of the body 16. The first portion 26 is slightly curved near the second end 37, the curved section following the curvature of the opening 32. The configured sidewall 33 also has a second portion 27 situated proximate the first end 36 and lateral side 34 of the body 16 that extends upwardly or transverse to the plane of the body 16. The second portion 27 is generally curved near the first end 36, the curved section following the curvature of the opening 32. The second portion 27 of the sidewall 33 is spaced from the first portion 26 of the sidewall 33 to provide a space or gap between the first and second portions 26, 27. The configured sidewall 33 further has a third portion 28 situated proximate the front 36 and lateral side 35 of the body 16 that extends upwardly or transverse to the plane of the body 16. The third portion is generally curved near the first end 36, the curved section following the curvature of the opening 32. The third portion 28 of the sidewall 33 is spaced from the second portion 27 of the sidewall 33 to provide a space or gap between the second and third portions 27, 28 such that the third portion 28 is generally opposite to the second portion 27. The height of the first, second and third portions 26, 27, 28 are preferably, but not necessarily, all the same. The configured sidewall 33 furthermore has a fourth portion 30 that is adjacent to the third portion 28 proximate the lateral side 35 of the body 16 that extends upwardly or transverse to the plane of the body 16. The fourth portion 30 is generally planar and has a height that is preferably, but not necessarily, less than the height of the first, second and third portions 26, 27, and 28. The configured sidewall moreover has a fifth portion 29 situated proximate the second end 37 and the lateral side 35 of the body 16 that extends upwardly or transverse to the plane of the body 16. The fifth portion is generally curved hear the second end 37, the curved section following the curvature of the opening 32. The fifth portion 29 of the sidewall 33 is adjacent the fourth portion 30. The height of the fifth portion 29 is preferably, but not necessarily, the same as the height of the first, second and third portions 26, 27, and 28. Because of the difference in height of the fourth portion 30 relative to the adjacent third and fifth portions 28, 29 a gap or space is defined between the third and fifth portions 28, 29. It should be appreciated that the nomenclature first, second, third, fourth, and fifth is arbitrary here and throughout.

Situated laterally along the first and second sidewalls 26, 27 is a first rail 20 that extends along the upper surface 18 of the body 16 from the raised superior surface 19 to the upwardly angled portion 31. Situated laterally along the third, fourth and fifth sidewalls 28, 29, 30 is a second rail 21 that extends along the upper surface 18 of the body 16 from the raised superior surface 19 to the upwardly angled portion 31. As best seen in FIG. 3, a first angled trough or channel 22 is formed at the lower outwardly lateral side of the first rail 20 adjacent the lateral side 34. A second angled trough or channel 23 is formed at the lower outwardly lateral side of the second rail 21 adjacent the lateral side 35. The first angled trough 22 forms part of an elongate lateral dovetail groove 64 between the assembled lower component 12 and the upper component 14 (see, e.g. FIG. 8, and below). The second angled trough 23 forms part of an elongate lateral dovetail groove 65 between the assembled lower component 12 and the upper component 14 (see, e.g. FIG. 8, and below).

The lower component 12 lastly has a plurality of spikes, projections, or the like 24 (collectively, spikes 24) situated on the lower or inferior side 17 of the body 16. As best seen in FIG. 5, the plurality of spikes 24 are linearly arranged laterally adjacent the opening 32. While only a single row of spikes 24 is provided on each side of the opening 32, more or less spikes may be provided in any pattern as desired. The shape of the spikes 24 may also be changed as desired.

Figure 8:
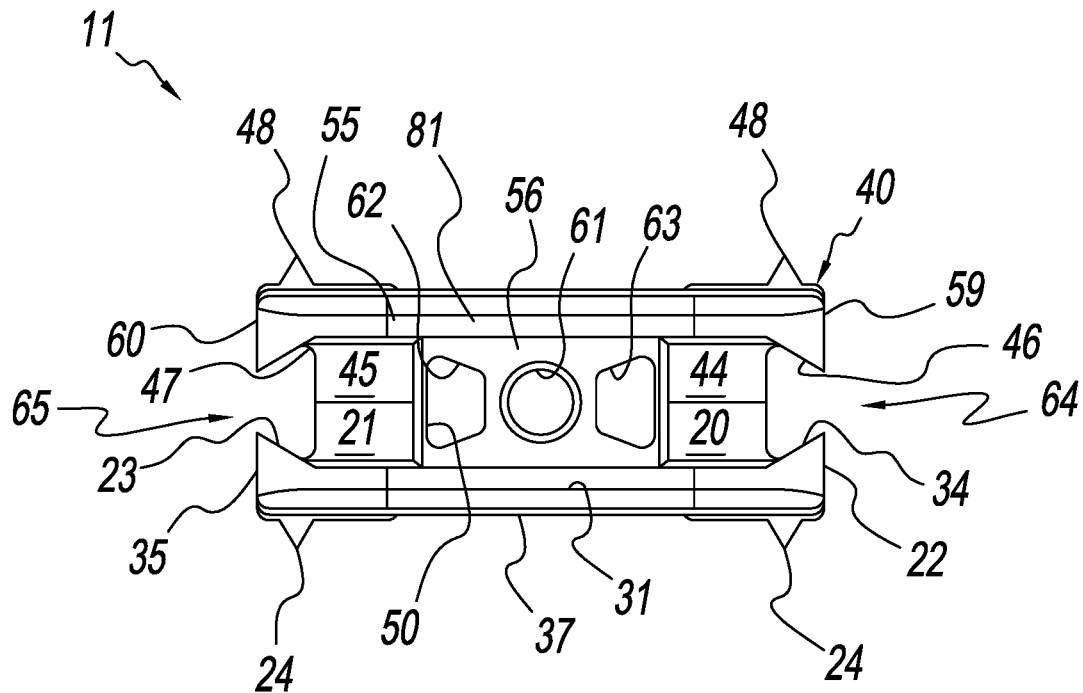
FIG. 8 is a lateral view of the assembled cage of the present spine cage implant.
Figure 9:
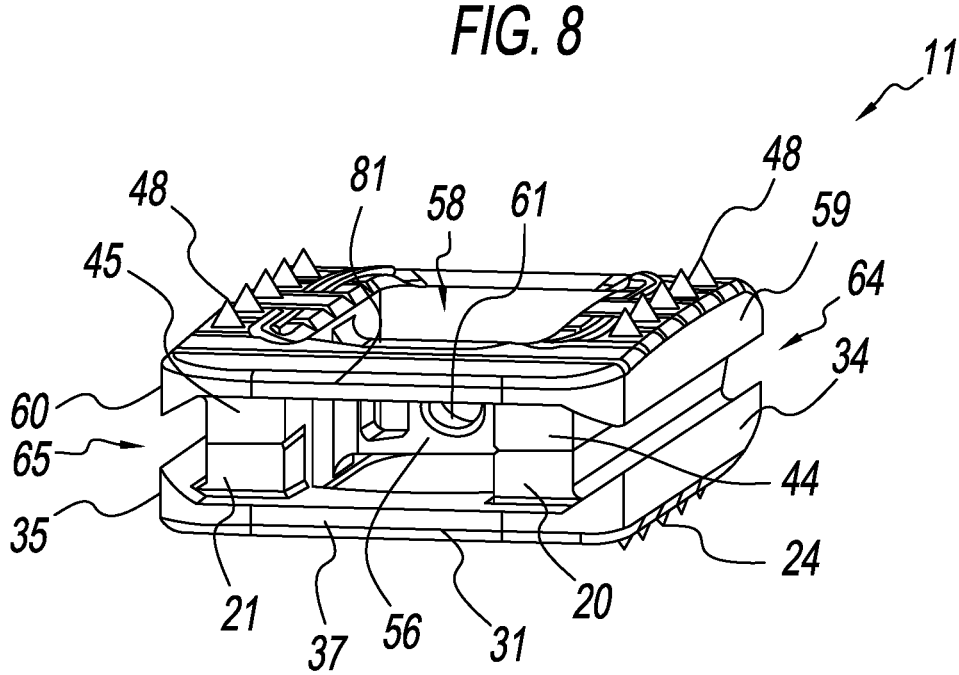
FIG. 9 is an upper lateral view of the assembled cage of the present spine cage implant.

The upper component 14 is characterized by a body 40 of a generally rectangular shape having a generally planar upper or superior surface 42 and a generally planar lower or inferior surface 41. The body 40 has a first, generally elongated lateral side 59 and a second, generally elongated lateral side 60, the nomenclature first and second being arbitrary. A first end 80 of the body 40 has a downwardly curved upper/superior front surface 43 with a generally planar lower/inferior surface 49, while a second end 81 of the body 40 has a generally planar upper/superior surface 55 and a downwardly angled lower portion 41 that meets with its generally planar lower/inferior surface 42. The body 40 further has a central opening, window or the like 82 that is generally oval in shape with a cross bar 56 extending between lateral sides of the oval opening 82 thereby dividing the oval opening 82 into a first opening 57 and a second opening 58, the nomenclature first and second being arbitrary. As best seen in FIG. 8, the cross bar 56 has a central bore 61 with a first configured window 62 on a first lateral side of the bore 61 and a second configured window 63 on a second lateral side of the bore 61, the windows allowing bone graft material to migrate between the openings 57, 58. The opening 82 is provided with a configured sidewall 50 that extends about a majority of the opening 82, with the exception of an area proximate the second end 81. The configured sidewall 50 extends downwardly or transverse to the plane of the body 40.

Situated laterally along the sidewall 50 adjacent the lateral end 59 of the body 40 is a third rail 44 that extends along the upper surface 41 of the body 40. Situated laterally along the sidewall 50 adjacent the lateral end 60 of the body 40 is a fourth rail 45 that extends along the upper surface 41 of the body 40. As best seen in FIG. 3, a third angled trough or channel 46 is formed at the upper outwardly lateral side of the third rail 44 adjacent the lateral side 59. A fourth angled trough or channel 47 is formed at the upper outwardly lateral side of the fourth rail 45 adjacent the lateral side 60. The third angled trough 46 forms part of the elongate lateral dovetail groove 64 between the assembled lower component 12 and the upper component 14 (see, e.g. FIG. 8, and below). The fourth angled trough 47 forms part of the elongate lateral dovetail groove 65 between the assembled lower component 12 and the upper component 14 (see, e.g. FIG. 8, and below).

As best seen in FIG. 4, the upper component 14 has four arced openings 51, 52, 53, 54 extending from the upper/superior surface to the lower/inferior surface of the body 40 that are situated about the opening 82. A first arced opening 51 is situated proximate to the lateral side 59 and the rear 81 of the body 40. A second arced opening 52 is situated proximate to the lateral side 59 and the first end 80 of the body 40. A third arced opening 53 is situated proximate to the lateral side 60 and the first end 80 of the body 40, opposite to the second arced opening 52. A fourth arced opening 54 is situated proximate to the lateral side 60 and the second end 81 of the body 40, opposite to the first arced opening 51. The first arced opening 51 corresponds in placement to the first portion 26 of the configured sidewall 33 of the lower component 12 when the upper and lower components 14, 12 are joined (assembled) such that the first portion 26 can be received in the first arced opening 51. The second arced opening 52 corresponds in placement to the second portion 27 of the configured sidewall 33 of the lower component 12 when the upper and lower components 14, 12 are joined (assembled) such that the second portion 27 can be received in the second arced opening 52. The third arced opening 53 corresponds in placement to the third portion 28 of the configured sidewall 33 of the lower component 12 when the upper and lower components 14, 12 are joined (assembled) such that the third portion 28 can be received in the third arced opening 53. The fourth arced opening 54 corresponds in placement to the fifth portion 29 of the configured sidewall 33 of the lower component 12 when the upper and lower components 14, 12 are joined (assembled) such that the fifth portion 29 can be received in the fourth arced opening 54.

The upper component 14 lastly has a plurality of spikes, projections, or the like 48 (collectively, spikes 48) situated on the upper or superior side 42 of the body 40. As best seen in FIG. 4, the plurality of spikes 48 are linearly arranged laterally adjacent the opening 82. While only a single row of spikes 48 is provided on each side of the opening 82, more or less spikes may be provided in any pattern as desired. The shape of the spikes 48 may also be changed as desired.

FIGS. 6-9 depict the upper and lower components 14, 12 joined or assembled together to form the cage 11 of the present expandable spinal cage implant. These figures depict the cage 11 at its smallest height, i.e. before expansion. The sidewall 50 of the upper component 14 fits inside the first, second, third, fourth, and fifth portions 26, 27, 28, 30, 29 of the sidewall 33 of the lower component 12. The first rail 20 of the lower component 12 and the third rail 44 of the upper component 14 abut one another such that their respective troughs 22, 46 form the elongated dovetail groove 64 along the lateral sides 34, 59 of the cage 11. The second rail 21 of the lower component 12 and the fourth rail 45 of the upper component 14 abut one another such that their respective troughs 23, 47 form the elongated dovetail groove 65 along the lateral sides 35, 60 of the cage 11. The configurations of the second end 37 of the lower component 12 and of the second end 81 of the upper component 14 define a reverse dovetail opening of the cage 11.

Figure 10:
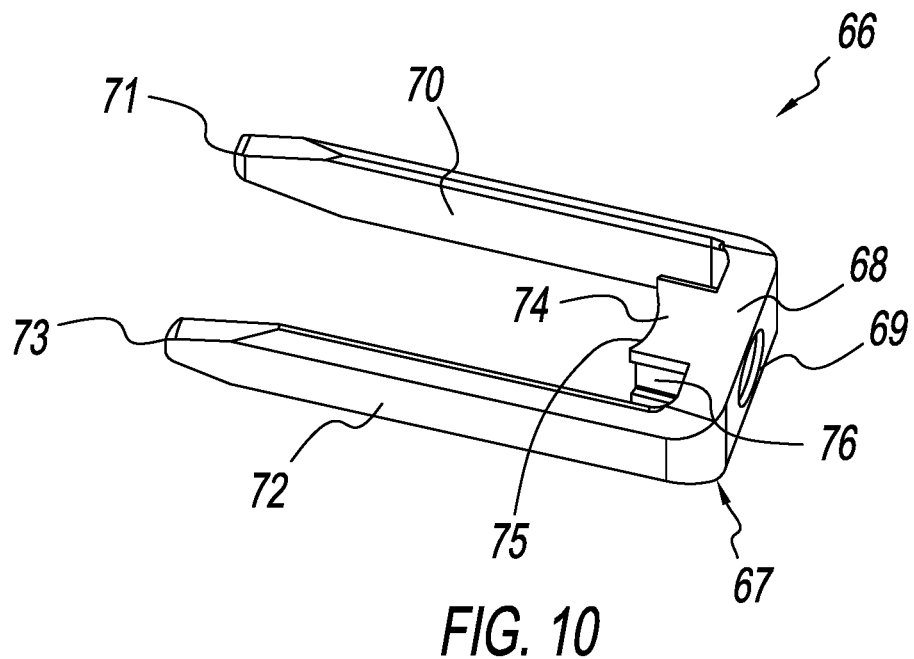
FIG. 10 is an isometric view of a third component of the present spine cage implant.
Figure 11:
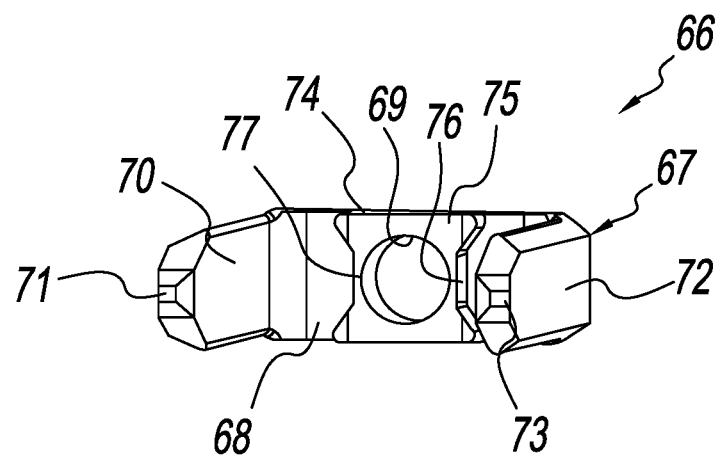
FIG. 11 is an isometric front lateral view of the third component shown in FIG. 10.

FIGS. 10-11 depict the expander 66 of the present expandable spine cage implant 10. The expander 66 is characterized by a generally elongated U-shaped body 67 having a base 68, a first elongated leg 70 extending from one lateral side of the base 68, and a second elongated leg 72 extending from another lateral side of the base 68. The base 68 has a boss 74 extending from an inner side thereof having an arced end 75. The boss 74 further includes a first angled cutout 76 on a first lateral side and a second angled cutout 77 on a second lateral side. A bore 69 extends through the base 68 and the boss 74. The first elongated leg 70 has a first height that is preferably, but not necessarily, constant along its length and terminates in a distal, arched end 71. The second elongated leg 72 has a second height that is preferably, but not necessarily, constant along its length and terminates in a distal, arched end 73. The first height of the first elongated leg 70 and the second height of the second elongated leg 72 are preferably, but not necessarily, the same. The base 68 is generally dovetail-configured for reception in the reverse dovetail opening of the cage 11.

Figure 12:
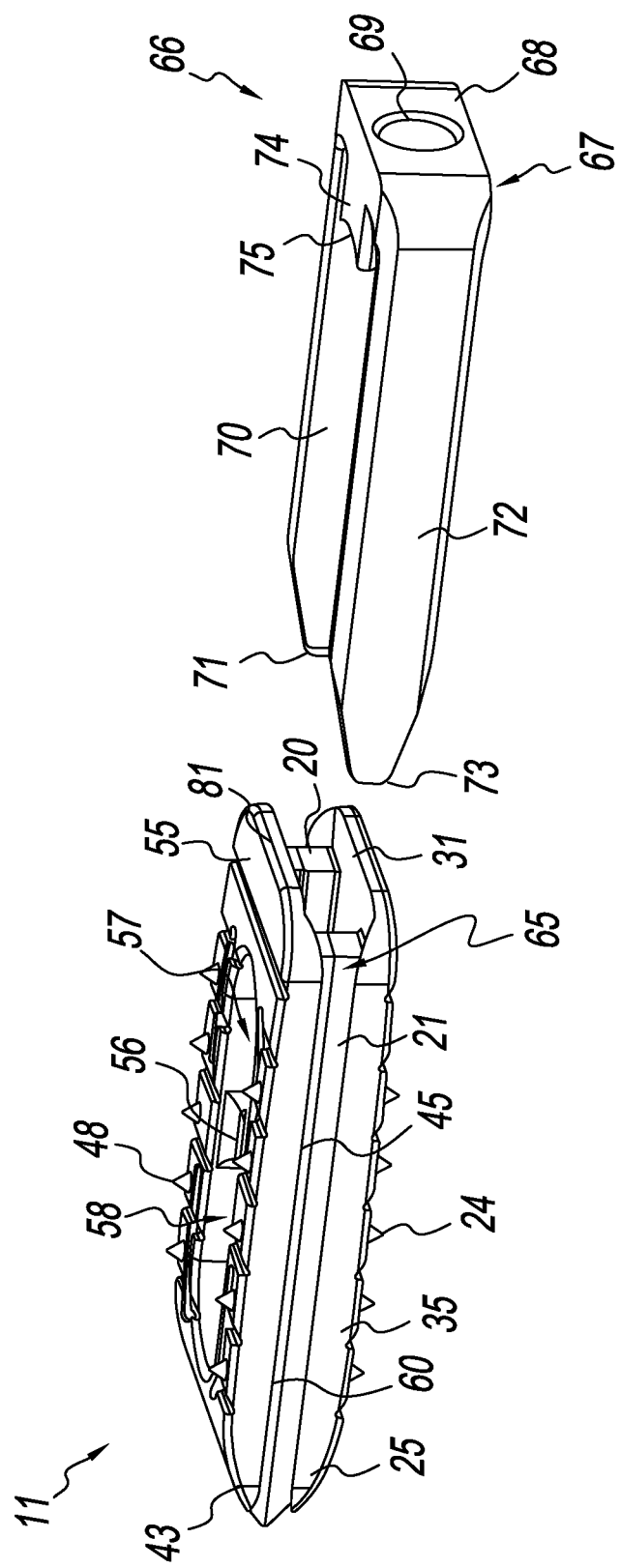
FIG. 12 is an exploded isometric view of the assembled cage and third component of the present spine cage implant.
Figure 13:
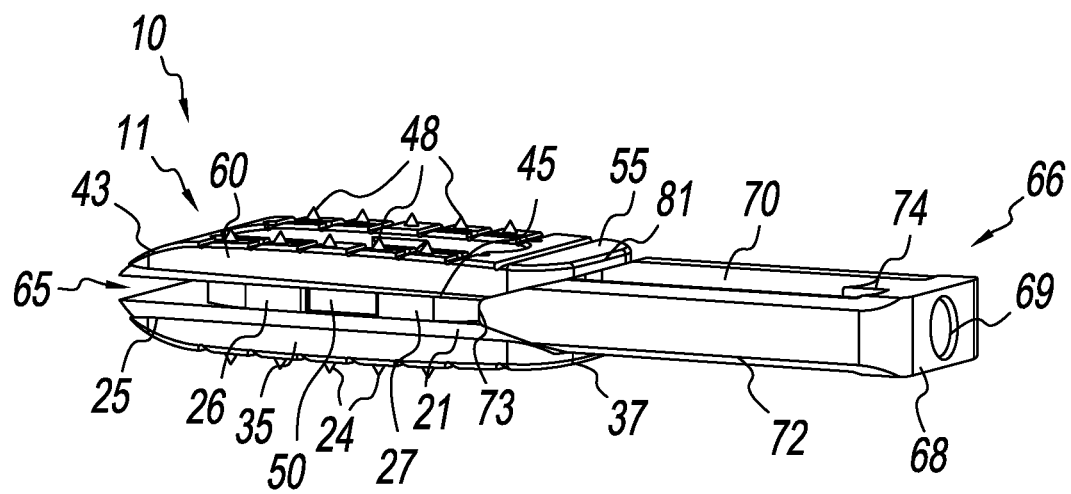
FIG. 13 is a partially exploded isometric view of the assembled cage and third component of the present spine cage implant.
Figure 14:
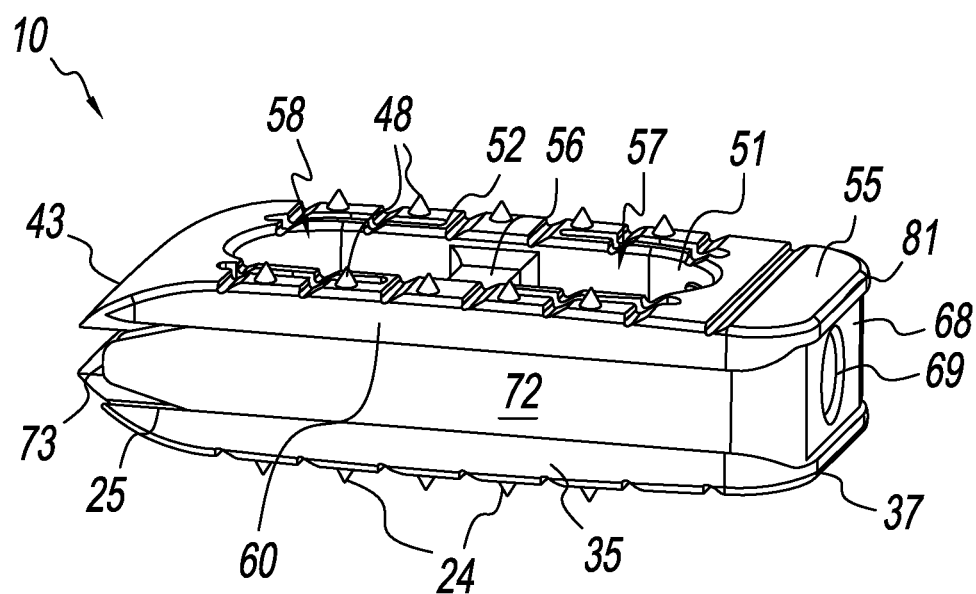
FIG. 14 is an isometric upper lateral view of the present spine cage implant.

FIGS. 12-14 depict the sequence of expanding the cage 11 once the cage 11 has been assembled (i.e. the upper and lower components 14, 12 have been joined). FIG. 12 depicts the alignment of the expander 66 relative to the cage 11. The legs 70, 72 are directed into respective elongated lateral dovetail grooves 64, 65. As the legs 70, 72 are received in the elongated lateral dovetail grooves 64, 65 (FIG. 13), the height of the legs 70, 72 separates or expands the upper and lower components 14, 12 relative to one another, the amount of expansion dependent upon the height of the legs 70, 72. FIG. 14 depicts the expander 66 fully received by the cage 11 with the dovetail base 68 of the expander 66 received in the reverse dovetail opening of the rear of the cage 11.

Figure 15:
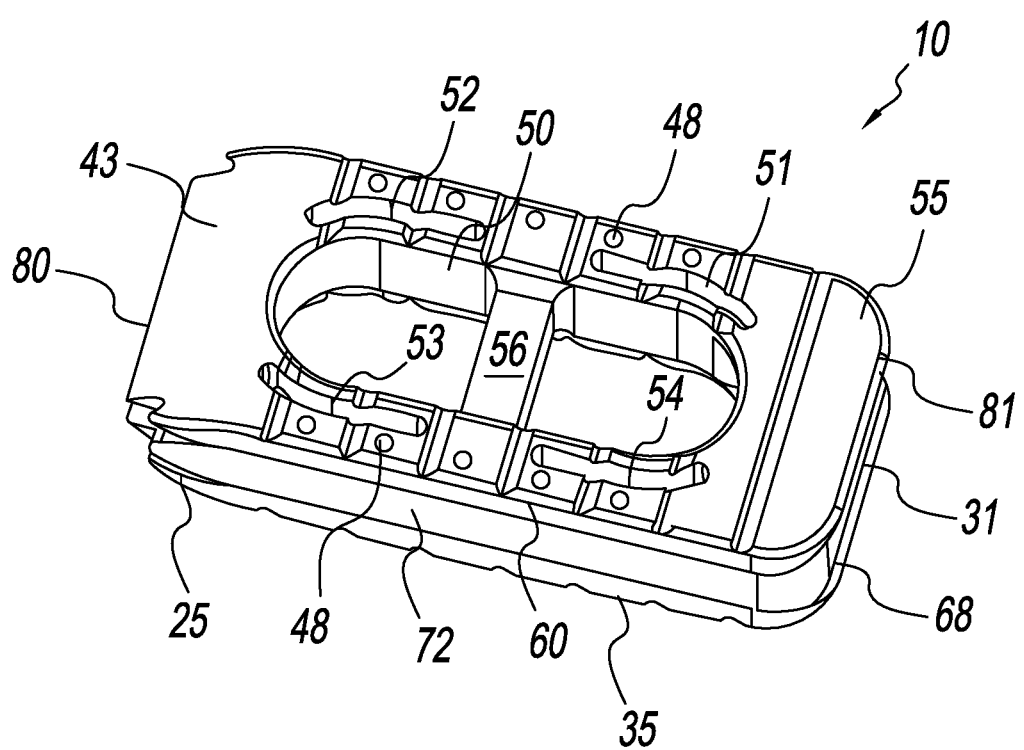
FIG. 15 is an isometric upper view of the present spine cage implant.
Figure 16:
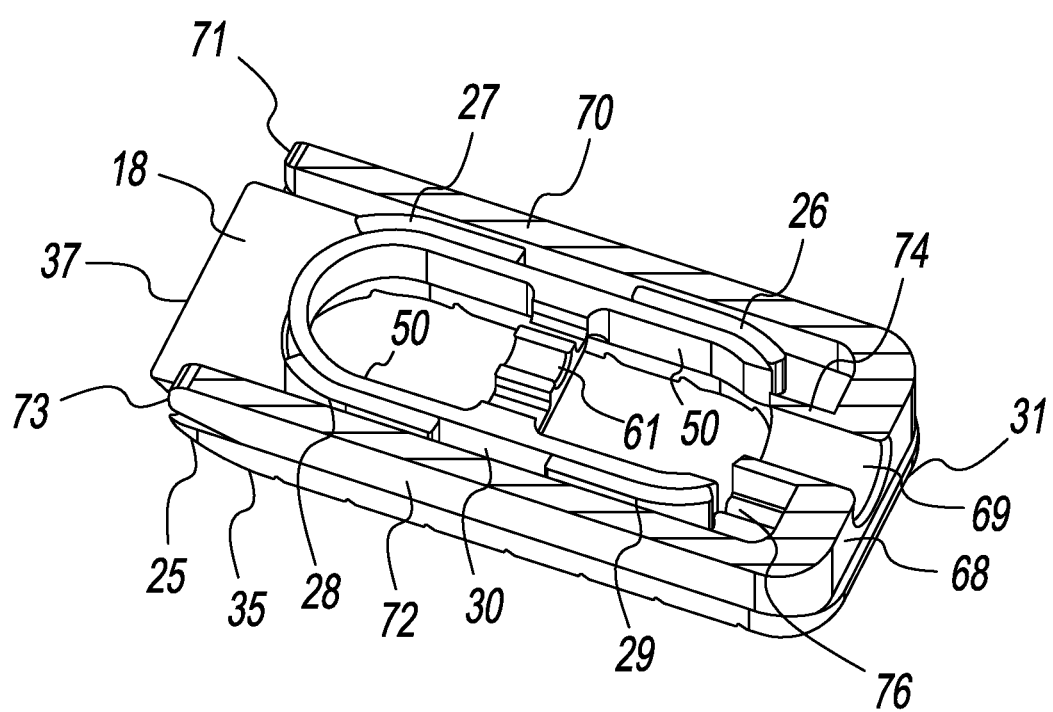
FIG. 16 is a sectional upper view of the second component on the third component, assembled, of the present spine cage implant.
Figure 17:
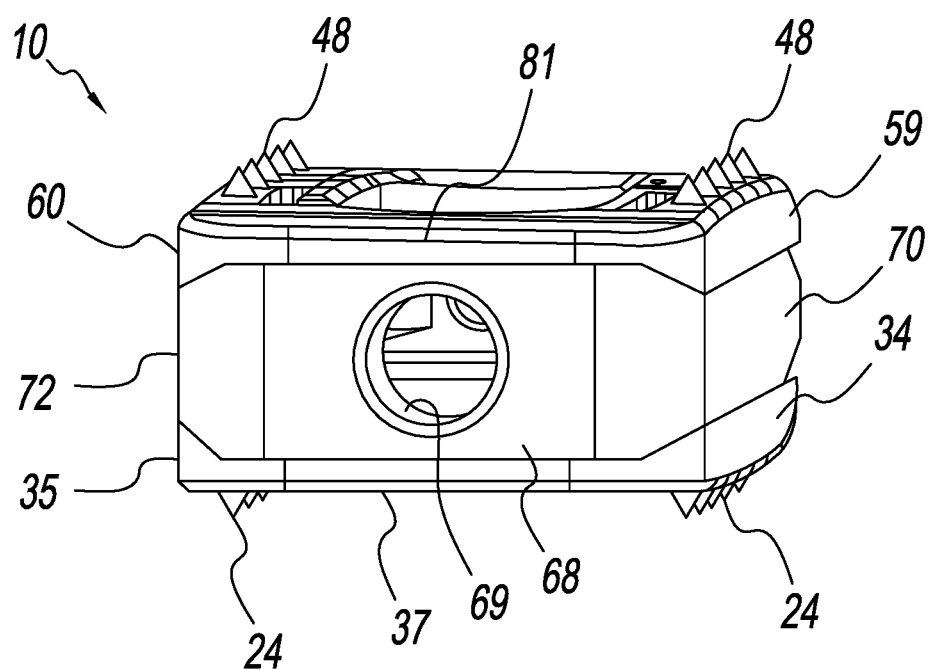
FIG. 17 is an isometric front view of the present spine cage implant.

FIG. 15 shows an upper view of the expanded spine cage implant 10. FIG. 17 is a rear view of the expanded spine cage implant 10. FIG. 16 is a sectional view of the expanded spine cage implant 10 cut along a plane of the expander 66 illustrating how the sidewalls 26-30 of the lower component 12 are received about the sidewall 50 of the upper component 14, and the expander 66 is received on the lower component 12.

The present expandable spine cage implant may be used in a lateral insertion procedure, an anterior insertion procedure, or a posterior insertion procedure.

It should be appreciated that dimensions of the components, structures, and/or features of the present expandable spine cage implant may be altered as desired within the scope of the present disclosure.

What is claimed is:

1. A lateral spinal interbody implant comprising:
   a first cage section comprising:
      a first plate having a first lateral side, a second lateral side, an interior surface and an exterior surface,
      a first central opening extending entirely through the first plate through the interior and exterior surfaces of the first plate,
      a plurality of arced apertures extending entirely through the first plate through the interior and exterior surfaces of the first plate, the plurality of arced apertures comprising a first arced aperture and a second arced aperture, the first arced aperture fully enclosed by a continuous periphery disposed at least partially between the first central opening and the first lateral side of the first plate, and the second arced aperture fully enclosed by a continuous periphery disposed at least partially between the first central opening and the second lateral side of the first plate, wherein each of the plurality of arced apertures is elongate along a length of the first central opening and curves at least partially around the first central opening;
   a second cage section comprising:
      a second plate having a first lateral side, a second lateral side, an interior surface and an exterior surface,
      a second central opening extending entirely through the second plate through the interior and exterior surfaces of the second plate, wherein the second central opening is surrounded by an inward facing surface, and
      a plurality of arced protrusions complementary to the plurality of arced apertures of the first cage section, the plurality of arced protrusions comprising a first arced protrusion and a second arced protrusion, the first arced protrusion at least partially disposed between the second central opening and the first lateral side of the second plate, the second arced protrusion at least partially disposed between the second central opening and the second lateral side of the second plate, wherein each of the plurality of arced protrusions is elongate along a length of the second central opening and forms an extension of the inward facing surface to share a common arc with the second central opening; and
   an expander configured to engage the first cage section and the second cage section;
   wherein the first and second cage sections are received together such that the plurality of arced protrusions of the second cage section are received by the plurality of arced apertures of the first cage section to create an interbody cage;
   wherein the interbody cage defines first and second dovetail grooves configured to receive at least a portion of the expander thereby determining a height of the implant.

2. The lateral spinal interbody implant of claim 1, wherein:
   the first cage section has a first lateral side slot, and a second lateral side slot;
   the second cage section has a first lateral side slot, and a second lateral side slot; and
   the first lateral side slot of the first cage section and the first lateral side slot of the second cage section form the first dovetail groove along a first lateral length of the interbody cage, and the second lateral side slot of the first cage section and the second lateral side slot of the second cage section form the second dovetail groove along a second lateral length of the interbody cage; and
   the expander includes an end, a first leg extending from the end and defining a first proximal end adjacent a first side of the end and a first distal end, and a second leg extending from the end and defining a second proximal end adjacent a second side of the end and a second distal end, the reception of the first leg in the first dovetail groove of the interbody cage and of the second leg in the second dovetail groove of the interbody cage adjusting the height of the implant in correspondence to heights of the first and second legs.

3. The lateral spinal interbody implant of claim 2, wherein:
   a first dovetail opening is formed at a first end of the first dovetail groove of the interbody cage;
   a second dovetail opening is formed at a second end of the second dovetail groove of the interbody cage;
   the first proximal end of the first leg of the expander having a first wedge shape complementary of the first dovetail groove; and
   the second proximal end of the second leg of the expander having a second wedge shape complementary of the second dovetail groove;
   the first wedge shape received in the first dovetail groove and the second wedge shape received in the second dovetail groove when the expander is received in the interbody cage.

4. The lateral spinal interbody implant of claim 3, wherein:
   the first distal end of the first leg is angled; and
   the second distal end of the second leg is angled.

5. The lateral spinal interbody implant of claim 4, further comprising:
   a plurality of expanders, each expander having different heights of the first and second legs.

6. The lateral spinal interbody implant of claim 4, wherein the exterior surface of the first plate includes first projections, and the exterior surface of the second plate includes second projections.

7. The lateral spinal interbody implant of claim 4, wherein the end of the expander has a central bore.

8. The lateral spinal interbody implant of claim 1, wherein the first cage section further comprises a sidewall protrusion along a portion of the perimeter of the first central opening, wherein the sidewall protrusion is configured to be received within the plurality of arced protrusions of the second cage section.

9. A lateral spinal interbody implant comprising:
a first cage section comprising:
a first outer end,
a second outer end opposite the first outer end,
an interior surface,
an exterior surface opposite the interior surface,
a first lateral side having a first lateral side slot extending substantially an entire length of the first cage section between the first outer end and the second outer end,
a second lateral side having a second lateral side slot extending substantially the entire length of the first cage section between the first outer end and the second outer end,
a first central opening extending through the interior and exterior surfaces of the first cage section and surrounded by the first outer end, the second outer end, the first lateral side, and the second lateral side, and
a plurality of arced apertures disposed through the interior and exterior surfaces of the first cage section and spaced about and substantially near the perimeter of the first central opening of the first cage section, wherein each of the plurality of arced apertures is elongate along a length of the first central opening and curves at least partially around the first central opening;
a second cage section comprising:
a third outer end,
a fourth outer end,
an interior surface,
an exterior surface opposite the interior surface,
a third lateral side having a third lateral side slot extending substantially an entire length of the second cage section between the third outer end and the fourth outer end,
a fourth lateral side having a fourth lateral side slot extending substantially the entire length of the second cage section between the third outer end and the fourth outer end,
a second central opening extending through the interior and exterior surfaces of the second cage section and surrounded by the third outer end, the fourth outer end, the third lateral side, and the fourth lateral side, and wherein the second central opening is surrounded by an inward facing surface, and
a plurality of arced protrusions projecting from the interior surface of the second cage section and spaced about the perimeter of the second central opening, wherein each of the plurality of arced protrusions is elongate along a length of the second central opening and forms an extension of the inward facing surface to share a common arc with the second central opening; wherein the first and second cage sections are aligned such that:
the plurality of arced apertures of the first cage section receive the plurality of arced protrusions of the second cage section;
the first lateral side slot of the first cage section and the third lateral side slot of the second cage section form a first dovetail channel; and
the second lateral side slot of the first cage section and the fourth lateral side slot of the second cage section form a second dovetail channel; and an expander comprising:
an end,
a first leg extending from the end and defining a first proximal end adjacent a first side of the end and a first distal end, and
a second leg extending from the end and defining a second proximal end adjacent a second side of the end and a second distal end, wherein the first leg is configured to be received by the first dovetail channel and the second leg is configured to be received by the second dovetail channel, thereby causing a height of the lateral spinal interbody implant to increase in correspondence to heights of the first and second legs of the expander.

10. The lateral spinal interbody implant of claim 9, wherein:
the first proximal end of the first leg of the expander having a first wedge shape complementary of the first dovetail channel;
the second proximal end of the second leg of the expander having a second wedge shape complementary of the second dovetail channel; and
the first wedge shape is received in the first dovetail channel and the second wedge shape is received in the second dovetail channel when the expander is received by the interbody implant.

11. The lateral spinal interbody implant of claim 10, wherein:
the first distal end of the first leg is angled; and
the second distal end of the second leg is angled.

12. The lateral spinal interbody implant of claim 11, further comprising:
a plurality of expanders, each expander having different heights of the first and second legs.

13. The lateral spinal interbody implant of claim 10, wherein the exterior surface of the first cage section includes first projections, and the exterior surface of the second cage section includes second projections.

14. The lateral spinal interbody implant of claim 11, wherein the end of the expander has a central bore.

15. The lateral spinal interbody implant of claim 9, wherein the first cage section further comprises a sidewall protrusion along a portion of the perimeter of the first central opening, wherein the sidewall protrusion is configured to be received within the plurality of arced protrusions of the second cage section.

16. An interbody implant for being implanted in a space between adjacent vertebrae of a spine; the interbody implant comprising:
an expandable cage comprising
a first component comprising an exterior surface, an interior surface, a first lateral side, a second lateral side, a first opening, and first and second arced apertures, the first opening and the first and second arced apertures extending through the exterior surface and the interior surface of the first component, the first and second arced apertures being at least partially disposed offset from and between the first lateral side of the first component and the first opening, wherein each of the first and second arced apertures is elongate along a length of the first opening and curves at least partially around the first opening;
a second component comprising an exterior surface, an interior surface, a first lateral side, a second lateral side, a second opening, and first and second arced protrusions, the second opening extending through the exterior surface and the interior surface of the second component, the first and second arced protrusions extending from the interior surface of the second component and being at least partially disposed offset from the first lateral side of the second component and between the second opening and the first lateral side of the second component, the first and second arced protrusions configured complementary to the first and second arced apertures of the first component, wherein the second opening is surrounded by an inward facing surface and each of the first and second arced protrusions is elongate along a length of the second opening and forms an extension of the inward facing surface to share a common arc with the second opening;

an expander comprising a first leg and a second leg, the first and second legs defining a height, wherein the expander is configured to be inserted between the first component and the second component after the first component and the second component are aligned and implanted in the space between the adjacent vertebrae of the spine;

wherein when the first component and the second component are aligned:

the first and second arced apertures of the first component receive the first and second arced protrusions extending upward from the second component; and the height of the first leg and the second leg determines an overall height of the interbody implant.

17. The interbody implant of claim 16 wherein:
the first component comprises a first angled channel and a second angled channel;
the second component comprises a third angled channel and a fourth angled channel;
the first and third angled channels define a first dovetail groove that extends substantially the entire length of the interbody implant and is configured to receive the first leg of the expander;
the second and fourth angled channels define a second dovetail groove that extends substantially the entire length of the interbody implant and is configured to receive the second leg of the expander.

18. The interbody implant of claim 16 wherein:
the first arced aperture and the second arced aperture each includes a linear portion and a curved portion; and
the first arced protrusion and the second arced protrusion each includes a linear portion and a curved portion, wherein the linear portions and the curved portions of the first and second arced protrusions are complementary to the linear portions and the curved portions of the first and second arced apertures of the first component.

19. The interbody implant of claim 16, wherein the first component further comprises a sidewall protrusion extending from the first opening away from the interior surface of the first component, wherein the sidewall protrusion is configured to be received within the first and second arced protrusions of the second component.

20. The interbody implant of claim 16, wherein the first component further comprises a crossbar that spans the first opening.

* * * * *